(12) United States Patent
Pinkos et al.

(10) Patent No.: US 7,759,531 B2
(45) Date of Patent: Jul. 20, 2010

(54) PROCESS FOR PREPARING 1,4-BUTANEDIOL

(75) Inventors: Rolf Pinkos, Bad Duerkheim (DE); Rudolf Erich Lorenz, Lambsheim (DE); York Alexander Beste, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/527,139

(22) PCT Filed: Mar. 14, 2007

(86) PCT No.: PCT/EP2007/052417
§ 371 (c)(1), (2), (4) Date: Aug. 13, 2009

(87) PCT Pub. No.: WO2008/098620
PCT Pub. Date: Aug. 21, 2008

(65) Prior Publication Data
US 2010/0016643 A1    Jan. 21, 2010

(30) Foreign Application Priority Data
Feb. 15, 2007   (EP)   ................... 07102460

(51) Int. Cl.
*C07C 29/17* (2006.01)
(52) U.S. Cl. ................................ 568/861
(58) Field of Classification Search ........... 568/861
See application file for complete search history.

(56) References Cited

U.S. PATENT DOCUMENTS

| | | | |
|---|---|---|---|
| 3,449,445 A | 6/1969 | Wetherill |
| 3,479,411 A | 11/1969 | Adam et al. |
| 3,954,669 A | 5/1976 | Broecker et al. |
| 4,048,116 A | 9/1977 | Voges et al. |
| 4,153,578 A | 5/1979 | De Thomas et al. |
| 4,288,640 A | 9/1981 | Schuster et al. |
| 4,599,466 A | 7/1986 | Mueller et al. |
| 5,015,788 A | 5/1991 | Toussaint et al. |
| 5,037,793 A | 8/1991 | Toussaint et al. |
| 5,068,468 A | 11/1991 | Schossig et al. |
| 6,262,317 B1 | 7/2001 | Becker et al. |
| 6,350,714 B1 | 2/2002 | Boettcher et al. |

FOREIGN PATENT DOCUMENTS

| | | |
|---|---|---|
| DE | 1 285 992 | 1/1969 |
| DE | 1 941 633 | 3/1971 |
| DE | 2 040 501 | 2/1972 |
| DE | 2 209 521 | 9/1973 |
| DE | 23 57 752 | 5/1975 |
| DE | 23 57 751 | 8/1975 |
| DE | 25 36 273 | 2/1977 |
| DE | 26 02 418 | 7/1977 |
| DE | 272 644 | 10/1989 |
| DE | 196 41 707 | 4/1998 |
| DE | 197 53 458 | 6/1999 |
| EP | 0 177 912 | 4/1986 |
| EP | 0 319 208 | 6/1989 |
| EP | 0 394 841 | 10/1990 |
| EP | 0 394 842 | 10/1990 |
| GB | 1 217 775 | 12/1970 |

OTHER PUBLICATIONS

Weissermel, Klaus et al., Industrielle Organische Chemie (Industrial Organic Chemistry), Wiley-VCH, 5$^{th}$ edition, pp. 110-111, (1998).

*Primary Examiner*—Elvis O Price
(74) *Attorney, Agent, or Firm*—Oblon, Spivak, McClelland, Maier & Neustadt, L.L.P.

(57) ABSTRACT

The present invention provides an integrated process for continuously preparing 1,4-butanediol, which comprises the following stages:
(I) reacting formaldehyde with acetylene in the presence of a copper catalyst at a pH of from 5 to 8 and a molar ratio of formaldehyde to acetylene of at most 2:1,
(II) intermediately buffering the resulting butynediol-containing aqueous mixture for from 0.1 to 100 h,
(III) hydrogenating the mixture obtained after the intermediate buffering and
(IV) distilling the hydrogenation product obtained in stage III to obtain 1,4-butanediol.

20 Claims, No Drawings

PROCESS FOR PREPARING 1,4-BUTANEDIOL

The invention relates to a process for preparing 1,4-butanediol from acetylene and formaldehyde via the intermediate of 1,4-butynediol.

The synthesis of 1,4-butynediol from acetylene and formaldehyde is widespread in industry and has been described, for example, in K. Weissermel, H.-J. Arpe, Industrielle organische Chemie [Industrial Organic Chemistry], 5th Edition, 1998, Wiley-VCH, pages 110 and 111). In addition to copper, the catalysts typically used may, if appropriate, comprise bismuth and also silicates (referred to hereinafter as $SiO_2$) or aluminum oxide. During the synthesis of 1,4-butynediol, a side reaction is the formation of oligomeric and polymeric substances (referred to hereinafter as cuprenes). These cuprenes, together with soluble and insoluble constituents of the catalyst used, typically get into the hydrogenation stage, in which 1,4-butenediol is formed initially and can be hydrogenated in a further hydrogenation step to the 1,4-butanediol intermediate, which is of greater significance than 1,4-butenediol.

The hydrogenation of 1,4-butynediol to 1,4-butanediol has been conducted for decades and described many times. For instance, U.S. Pat. No. 5,068,468 discloses the hydrogenation of 1,4-butanediol over solid supported nickel-copper catalysts, while U.S. Pat. No. 4,153,578 describes a two-stage process for hydrogenating 1,4-butynediol over suspended Raney nickel-molybdenum catalysts at a pressure of 21 bar. DD-A 272 644 discloses the suspension hydrogenation of aqueous butynediol over nickel-$SiO_2$ catalysts, and EP-B 0 319 208, DE-A 19 41 633 and DE-A20 40 501 disclose general hydrogenation processes which are applicable to 1,4-butynediol among other substances.

Cuprenes and catalyst constituents from the butynediol synthesis disrupt the hydrogenation of 1,4-butynediol to 1,4-butenediol or 1,4-butanediol and significantly impair the hydrogenation result. For instance, cuprenes are deposited on the catalyst and the pores and hinder the contact of butynediol with the catalyst surface, with the consequence that the reaction becomes slower and the pressure drop over the reactor rises. Catalyst components such as copper, bismuth and/or $SiO_2$ are likewise deposited on the catalyst and, together with the cuprenes, change the catalyst activity and selectivity.

These disadvantageous effects may, in addition to a buildup in the pressure difference, also be monitored by the formation of the butanol by-product and further components which disrupt the purity of the butanediol, since their formation is accelerated by the aforementioned catalyst poisons.

The simple purification of 1,4-butynediol, for example by filtration, is hardly possible, since especially the cuprenes and $SiO_2$ are present partly in colloidal or ultrafinely distributed form and thus rapidly block common filters, so that the filters either constantly have to be changed or back-flushed in a complicated manner.

It is an object of the invention to provide an industrial scale process with which, especially in plants with large capacities, 1,4-butanediol can be produced in a very simple and economically viable manner without the catalysts used losing activity rapidly or needing to be regenerated or exchanged. In addition, 1,4-butanediol should be preparable reliably in the purity required by the market. In general, a 1,4-butanediol content of at least 99.5% is required, and, in addition, the contents of 2-methyl-1,4-butanediol may be max. 0.4% and that of 2-(4-hydroxybutoxy)tetrahydrofuran, referred to hereinafter as acetal, may be max. 0.15%.

It has now been found that, surprisingly, this object is achieved by an integrated process for continuously preparing 1,4-butanediol, which comprises the following stages:

(I) reacting formaldehyde with acetylene in the presence of a copper catalyst at a pH of from 5 to 8 and a molar ratio of formaldehyde to acetylene of at most 2:1, (II) intermediately buffering the resulting butynediol-containing aqueous mixture for from 0.1 to 100 h, (III) hydrogenating the mixture obtained after the intermediate buffering and (IV) distilling the hydrogenation product obtained in stage III to obtain 1,4-butanediol.

The acetylene to be used for stage (I) of the process according to the invention may, for example, originate through hydrolysis of calcium acetylide (carbide), partial combustion of hydrocarbons such as methane, or from crackers. According to the invention, it is reacted with formaldehyde at a pressure (absolute) of from 0.5 to 50 bar, preferably from 0.8 to 25 bar, more preferably from 0.9 to 10 bar. Acetylene preferably has a purity of >99%.

Formaldehyde is used as an aqueous solution in stage (I) of the process according to the invention and stems generally from the (partial) oxidation of methanol. The formaldehyde content in water may, for example, be between 10 and 80% by weight; the content is preferably between 25 and 65% by weight; it is more preferably between 30 and 60% by weight. The purity of the formaldehyde (calculated without water) should be above 95%. Typically, the remainder to 100% consists predominantly of methanol, but it is advantageous when its content is at a minimum, i.e. the purity of the formaldehyde is significantly above 95%. Further secondary constituents, for example formic acid, are advantageously in the region of <0.1%.

It has been recognized in accordance with the invention that it is preferred for the very efficient reaction of acetylene with formaldehyde that free acetylene is always present through the entire reaction zone for stage (I), i.e. even toward the end of the reaction zone (reactor outlet). In the context of this invention, free acetylene is understood to mean acetylene which is present in dissolved or gaseous form in the reactor for the reaction of acetylene with formaldehyde. This means that the molar ratio of formaldehyde:acetylene in the reaction is preferably at most 2:1. The presence of free acetylene surprisingly prevents the premature aging or destruction of the catalyst. Preference is therefore given to either using a molar ratio of acetylene to formaldehyde of at least 0.5:1 as early as at the start of the reaction or to metering in additional acetylene at various points in the reaction zone during the reaction. More preferably, the molar ratio of acetylene to formaldehyde in the reaction zone(s) is from 0.501:1 to 0.55:1.

In stage (I), the reaction of acetylene with formaldehyde is performed typically at temperatures of from 30 to 130° C. Preference is given to from 50 to 100° C., particular preference to from 65 to 90° C.

Residence times of from 0.5 to 200 h, preferably from 1 to 100 h, more preferably from 5 to 50 h, are established.

The catalysts used for the reaction of acetylene with formaldehyde are known per se, and suitable catalysts are described, for example, in DE-A 22 09 520, DE-A 22 09 521, DE-A 23 57 752, DE-A 23 57 751, DE-A 26 02 418, DE-A 197 53 458.

In stage (I) of the process according to the invention, preference is given to using catalysts which comprise copper and further components such as bismuth. Particular preference is given to using the catalysts which are known from DE-A 26 02 418 and comprise bismuth and copper on a silicon dioxide support.

The reaction of acetylene and formaldehyde can be effected in one or more reactors connected in parallel or series. The catalysts used may be used in suspension, in a fluidized bed and/or a fixed bed, embodiments with different methods being possible in the individual reactors when using a plurality of reactors.

The reaction of formaldehyde and acetylene (stage (I)) by means of a fixed bed can be conducted in trickle mode or liquid phase mode. It is preferred in this case to utilize at least two successive reactors, since this eases the reaction and ensures higher conversions. Each reactor alone or all reactors together may have an external gas and/or liquid circulation, for example a ratio of feed to liquid circulation of 1 to 20. This allows, for example, the temperature control to be simplified and/or a maximum acetylene concentration to be ensured. When a plurality of reactors are used, they can be operated at different temperature and pressure levels. In addition, when one or more reactors are operated in liquid phase mode, this ensures that the catalyst filling is raised somewhat, which firstly leads to a reduction in the weight borne on the catalyst and secondly ensures better mixing.

During the reaction of acetylene with formaldehyde, a suitable adjustment of the pH allows damage to the catalysts to be prevented. The pH for stage (I) is from 4 to 10, preferably from 5 to 8, more preferably from 6 to 8. The pH can be adjusted by adding organic or inorganic acids or bases or substances which have an acidic or basic reaction in water. The addition can be effected, for example, into the feed stream and/or the circulation stream. When a plurality of reactors are used, each reactor alone can be pH-regulated. Acidic or acid-acting additives are, for example, sulfuric acid, phosphoric acid, hydrochloric acid, formic acid, acetic acid, esters such as ethyl formate or gamma-butyrolactone. In general, the metered addition of bases or base-acting substances is more significant, since side reactions of formaldehyde form acid-acting substances, for example formic acid. Examples thereof are hydroxides, carbonates, hydrogencarbonates, formates, acetates, oxalates of alkali metals and alkaline earth metals, for example sodium hydroxide, potassium hydroxide, sodium carbonate, sodium hydrogencarbonate, potassium carbonate or potassium hydrogencarbonate. These substances are preferably introduced as aqueous solutions. It is also possible to use mixtures of the basic substances or of the acidic substances. Preference is given to using aqueous sodium hydroxide or potassium hydroxide solution.

Although the pH regulation protects the catalysts for stage (I), salts which typically remain in the reaction effluent of the reaction of acetylene with formaldehyde are introduced into the reaction system, since a removal, for example by distillation or ion exchange, is very complicated and would make industrial scale use of the process less economically attractive. The reaction effluent of stage (I) of the process according to the invention comprises, as well as from 10 to 90% by weight of 1,4-butynediol, the salts mentioned, water, unconverted formaldehyde, unconverted acetylene, relatively small amounts of intermediates such as propynol, products from the reaction of acetylene and formaldehyde, some of which are of macromolecular character. For example, these are formaldehyde acetals based on methanol, propynol and 1,4-butynediol, and also oligomeric and polymeric components, some of which are dissolved, present as colloids or discernible as solids with the naked eye, for example cuprenes (Chemie und Technik der Acetylen-Druck-Reaktionen [Chemistry and Technology of Pressurized Acetylene Reactions], Walter Reppe, Weinheim, Verlag Chemie, 1951). It is also possible for catalyst constituents to be present in dissolved, colloidal and/or solid form. Depending on the catalyst, these are, for example, components which comprise copper, bismuth or catalyst support materials, for example aluminum oxide hydrates, silicates, titanates and the like.

In accordance with the invention, it has now been recognized that it is advantageous to introduce the reaction effluent of stage (I) into an intermediate buffer in which the mean residence time is very high; technically relevant residence times are from 0.1 to 100 h, preferably from 0.5 to 50 h, more preferably from 1 to 30 h. In this application, intermediate buffer is understood to mean a region which is spatially separate from the reactor of stage (I) and the hydrogenation reactors of stage (III) and may be any vessel, a tank, a stirred apparatus or a pipeline in which the reaction effluent remains for the inventive residence time. Preference is given to using a tank or a vessel which may have pumped circulation or stirring. Advantageously, the withdrawal point for the feed into stage (III) is above the lowest point in the tank or vessel. This has the effect that solids can settle and hence do not get into the hydrogenation.

The intermediate buffering in stage (II) of the process according to the invention of the 1,4-butynediol-comprising aqueous product stream, which has a 1,4-butynediol content of, for example, from 10 to 90% by weight, preferably from 30 to 70% by weight and more preferably from 40 to 60% by weight, is typically at temperatures of from 20 to 100° C., preferably at 40 and 90° C., more preferably from 50 to 80° C. Advantageously, the intermediate buffering is performed under inert gas atmosphere. The inert gases used may, for example, be nitrogen, carbon dioxide or the noble gases; preference is given to using nitrogen. The pressure for the intermediate buffering is uncritical per se, but preference is given to performing the intermediate buffering at from 0.8 to 20 bar. The preferred temperature range is between 40 and 90° C., more preferably from 50 to 80° C.

In a particularly preferred embodiment, in accordance with the invention, the reaction effluent of stage (I), before the intermediate buffering (II), is freed of excess acetylene at from 0 to 100° C. and 0.1-1 bar (absolute) in at least one distillation stage (Ia). The acetylene removed can be recycled into stage (I). Moreover, in a preferred embodiment, excess formaldehyde can additionally be removed together with water and/or intermediates such as propynol by distillation, for example at 80-100° C. and 0.1-1 bar (absolute), and recycled into stage (I).

However, it is also possible to conduct the reaction effluent from stage (I) directly into the intermediate buffer and, after the intermediate buffering (stage II) and before the hydrogenation to 1,4-butanediol (stage III) to distill it in at least one distillation stage (distillation stage IIa) under the conditions specified above for the distillation stage (Ia). After distillation stage (IIa), a further intermediate buffer can be used under the conditions specified above for stage (II).

It has been found that, surprisingly, the intermediate buffering of the butynediol-comprising aqueous product stream which may have been distilled beforehand makes the subsequent hydrogenation to 1,4-butanediol significantly more economically viable, since firstly the catalyst lifetime (catalyst on-stream time) and secondly the yield of 1,4-butanediol and also its purity are improved.

Subsequently, the mixture obtained after the intermediate buffering (II) is catalytically hydrogenated (stage III).

Suitable catalysts for the hydrogenation of 1,4-butynediol are those which are capable of hydrogenating C—C triple and double bonds to single bonds. They generally comprise one or more elements of transition group I, VI, VII or VIII of the Periodic Table of the Elements, preferably the elements copper, chromium, molybdenum, manganese, rhenium, iron, ruthenium, cobalt, nickel, platinum and palladium. Particular preference is given to using catalysts which comprise at least one element selected from copper, iron, nickel, platinum and palladium.

The metal content of these catalysts is generally between 0.1 to 100% by weight, preferably from 0.2 to 95% by weight, more preferably from 0.5 to 95% by weight.

The catalyst preferably additionally comprises at least one element selected from the elements of main group II, III, IV and VI, of transition group II, III, IV and V of the Periodic Table of the Elements, and the lanthanoids as a promoter for enhancing the activity.

The promoter content of the catalyst is generally up to 25% by weight, preferably 0.001-15% by weight, more preferably 0.01-13% by weight.

The catalysts used may be precipitation catalysts, supported catalysts or Raney-type catalysts, whose preparation is described, for example, in Ullmanns, Encyclopädie der technischen Chemie [Encyclopedia of Technical Chemistry], 4th Edition, 1977, Volume 13, pages 558-665.

The support materials used may be aluminum oxides, titanium oxides, zirconium dioxide, silicon dioxide, aluminas, for example montmorillonites, silicates such as magnesium silicates or aluminum silicates, zeolites and activated carbons. Preferred support materials are aluminum oxides, titanium dioxides, silicon dioxide, zirconium dioxide and activated carbon. It will be appreciated that it is also possible to use mixtures of different support materials as supports for catalysts usable in the process according to the invention.

These catalysts may be used either as shaped catalyst bodies, for example as spheres, cylinders, rings, spirals, or in the form of powders. Preference is given to using the catalysts in the form of shaped bodies. Suitable catalysts for the hydrogenation are, for example, from DE-A 12 85 992, DE-A 25 36 273, EP-A 177 912, EP-A 394 841, EP-A 394 842, U.S. Pat. No. 5,068,468, DE-A 1 641 707 and EP-A 922 689, particular preference being given to the catalysts which are known from EP-A 394 841 and have a content of from 20 to 75% by weight of nickel oxide, from 10 to 75% by weight of zirconium dioxide and from 5 to 50% by weight of copper oxide.

It is also possible to use catalysts of the Raney type, for example Raney nickel, Raney copper, Raney cobalt, Raney nickel/molybdenum, Raney nickel/copper, Raney nickel/chromium, Raney nickel/chromium/iron or rhenium sponge, for stage (III) of the process according to the invention. Raney nickel/molybdenum catalysts can be prepared, for example, by the process described in U.S. Pat. No. 4,153,578. These catalysts are also sold, for example, by Degussa, 63403 Hanau, Germany. A Raney nickel-chromium-iron catalyst is sold, for example, under the trade name of catalyst type 11 112 W® by Degussa.

When precipitated or supported catalysts are used, they are reduced before the start of the reaction at 150 and 500° C. in a hydrogen or hydrogen/inert gas stream. This reduction can be performed directly in the hydrogenation reactor. If the reduction is performed in a separate reactor, the catalysts may be surface-passivated with oxygenous gas mixtures at, for example, 30° C. before the deinstallation. In this case, the passivated catalysts can be used in the hydrogenation reactor activated before use in a nitrogen/hydrogen stream at, for example, 180° C. or else without activation.

The catalysts can be used in a fixed bed or in suspension. When the catalysts are arranged in the form of a fixed bed, the reactor is operated in trickle mode or in an upward cocurrent of liquid and gas.

Suspended catalysts are used with a particle size generally of from 0.1 to 500 μm, preferably from 0.5 to 200 μm, more preferably from 1 to 100 μm. When suspended catalysts are used in packed bubble columns, operation is likewise effected with an upward cocurrent of liquid and gas, such that the liquid and not the gas is present as the continuous phase.

The ratio of gas rate leaving the reaction vessel to gas rate supplied which is to be maintained in accordance with the invention in the case of fixed bed catalysts and in the case of catalysts suspended in the reaction medium in packed bubble columns can be adjusted in a simple manner by metering in the appropriate amount of hydrogen either as fresh gas or, preferably from a technical point of view, cycle gas and only replacing the hydrogen loss caused by chemical consumption and offgas with fresh hydrogen.

The molar ratio of fresh hydrogen to 1,4-butynediol is at least 2:1, preferably between 2.01 to 3:1. The fresh hydrogen is preferably added upstream of the reaction zone, but it is also possible, if appropriate, additionally to feed in hydrogen at other points, for example by means of inserted tubes into the catalyst region and/or, in the case of use of a plurality of reactors, upstream of and/or into the particular reactor. When hydrogenation with cycle gas is employed, the molar ratio of hydrogen (sum of fresh gas and cycle gas hydrogen) to the sum of 1,4-butynediol, 1,4-butenediol and 1,4-butanediol is at least 3:1, preferably from 4:1 to 100:1, more preferably from 5:1 to 70:1. Cycle gas may be distributed over all hydrogenation reactors used, or only over individual stages, for example the so-called main reactors. It is possible for a gas, liquid separator to be downstream of each reactor, from which gas for the cycle gas can be withdrawn.

The process according to the invention is performed over fixed bed catalysts with cycle gas mode, i.e. the gas leaving the reactor is recycled in circulation, if appropriate after supplementation with fresh hydrogen, through a compressor into the reactor. It is possible to conduct the entire amount of cycle gas or a portion thereof through a motive-jet compressor. In this preferred embodiment, the cycle gas compressor is replaced by an inexpensive nozzle. The work of compression is introduced through the liquid likewise conducted in circulation. The required pressure increase of the liquid to operate the motive-jet compressor is from about 3 to 5 bar.

For the performance of the process according to the invention with a catalyst suspended in the reaction medium, suitable apparatus includes jet nozzle reactors, stirred tanks and bubble columns with packings which have a packing surface area of at least 500, preferably from 1000 to 2000 m$^2$/m$^3$. Jet nozzle reactors can be used in various designs when they can ensure the high mass transfer, which is essential for the invention, from the gas phase to the liquid comprising the suspended catalyst particles by virtue of a sufficiently high energy input which, as experience has shown, is above 2 kW/m$^3$. Particularly suitable reactors are jet nozzle reactors which are equipped with a momentum exchange tube. An industrially widespread design of a jet nozzle reactor is, for example, the reactor described in EP-A 0 419 419. At values of the energy input of from 3 to 5 kW/m$^3$, this reactor enables separation of the gas phase even in simple separators without any need to utilize additional apparatus such as foam centrifuges or cyclones.

Stirred vessels are suitable for the performance of the process according to the invention only when the energy input is in a range of from 2 to 10 kW/m$^3$.

Jet nozzle reactors with suspended catalysts require volume-based energy inputs of more than 2 kW/m$^3$, preferably 3-5 kW/m$^3$.

For the performance of the process according to the invention on the industrial scale, preference is given to performing the hydrogenation in at least two stages (main hydrogenation and post-hydrogenation), in which case preference is given to using at least one so-called main reactor and at least one so-called postreactor.

The majority of the reaction will preferably take place in the main reactor or in the main reactors. Typically, the conversion of all double and triple bonds to be hydrogenated in the main reactor or in the main reactors is between 60 and 99.99%, preferably between 80 and 99.99%, more preferably from 90 to 99.99%. In this application, double and triple bonds to be hydrogenated mean compounds which still comprise C—C triple or double bonds and C—O double bonds, and compounds which contain C—O double bonds are, for example, butyraldehyde and 4-hydroxybutyraldehyde or their acetals. Particular preference is given to having such a high conversion in the main reactor that the residual hydrogenation can be performed without cooling in the post-reactor or the post-reactors. As is technically customary, the cooling during the main hydrogenation can be ensured with internal or external heat exchangers. In the case of external heat exchangers, a substream of the hydrogenation effluent, which, after cooling, is recycled back into the hydrogenation mixed with fresh feed, is used. For example, the ratio of circulation to feed is from 2:1 to 50:1, preferably from 3:1 to 30:1, more preferably from 5:1 to 15:1.

The hydrogenation in the main reactor(s) (main hydrogenation) is performed at temperatures between 30 and 300° C., preferably between 50 and 250° C. and more preferably between 70 and 220° C. When the hydrogenation is performed in a fixed bed, the hydrogenation pressure in the main hydrogenation is between 25 and 350 bar, preferably between 100 and 330 bar, more preferably between 150 and 300 bar. When suspended catalysts are used, the reaction pressure is between 2 and 150 bar, preferably between 5 and 100 bar, more preferably between 10 and 65 bar.

The hydrogenation in the post-reactor(s) (post-hydrogenation) can proceed under the same temperature and pressure conditions as those described for the main hydrogenation.

However, it is also possible to perform the post-hydrogenation at temperatures higher by from 10 to 50° C. The inlet temperature of the first post-reactor is preferably equal to the outlet temperature of the main reactor. When the inlet temperature of the post-reactor is to be higher or lower than the outlet temperature of the main reactor, the stream to the post-reactor is additionally heated or cooled. For cooling, preference is given to using a substream from the circulation stream of the main reactor after it has been cooled.

In a preferred embodiment of the main hydrogenation in fixed bed mode, the hydrogenation is performed in at least two parallel reactors. After prolonged operation of the hydrogenation, the hydrogenation catalyst is covered by the salts which have formed in the 1,4-butynediol synthesis, colloidal and solid components, the hydrogenation catalyst, and this leads to an increased rise in pressure difference in the case of fixed bed catalysts and to reduced catalyst activity and selectivity in the case of suspended catalysts. Especially when expensive catalysts are used, it is indispensable for an economically viable process to achieve a maximum catalyst lifetime. If the catalysts were to be exchanged after an increased pressure drop and/or a declining activity and selectivity have been established, the catalyst costs would be too high. The catalysts are therefore deinstalled from the reactors, washed with water and then reused. When a plurality of parallel reactors are available, the hydrogenation can continue without the overall process having to be shut down.

It has now been found that, surprisingly, the catalysts have a higher lifetime when the product obtained from the 1,4-butynediol synthesis is intermediately buffered in accordance with the invention. The process according to the invention significantly prolongs the time between the wash cycles, and the catalysts can be reused significantly more frequently after the washing operation. In addition, the overall yield and the purity of the 1,4-butanediol obtained is higher.

It is advantageous to monitor the pH during the hydrogenation. For the pH adjustment, the same acid- or base-acting substances can be used as have been described above in the description of the reaction of acetylene and formaldehyde (stage I). The pH range of the hydrogenation is generally between 5 and 11, preferably between 6 and 9, more preferably between 6.5 and 8. The pH adjustment is advantageous in order firstly to ensure the lifetime of the catalysts used, since the catalyst supports can dissolve in the acidic or basic range in particular, and secondly in order to suppress side reaction. For example, the formation of 2-methyl-1,4-butanediol is attributable to the reaction of formaldehyde and 4-hydroxybutyraldehyde (an intermediate of the hydrogenation), in particular under basic conditions. Moreover, the pH monitoring prevents corrosion on materials in the reactor and pipelines.

In embodiments in which at least one post-reactor is used, the aim in this post-reactor is the residual conversion of double and triple bonds which remain in the main hydrogenation and are to be hydrogenated. Preference is given to achieving a conversion of at least 99.95%, particular preference to achieving a conversion of at least 99.99%. However, the conversion in the post-reactor is most preferably complete (100%). The post-hydrogenation in the post-reactor or in the post-reactors is preferably performed over fixed bed catalysts. Trickle mode or upward mode can be selected, preference being to given to working without liquid recycling.

Since colloidal and solid impurities from the butynediol synthesis are for the most part precipitated in the main hydrogenation, washing of the catalyst in the post-hydrogenation is usually not necessary, but is necessary at least significantly less often.

The product stream which stems from the post-hydrogenation is passed into a separator in which gas and liquid phase separate. The gas phase comprises predominantly hydrogen. When hydrogenation is effected with cycle gas, this separator is preferably operated at the same pressure as the hydrogenation, in order that the gas withdrawn therefrom need not additionally be compressed. A portion of the gas stream can be disposed of as offgas.

The liquid phase of the separator can be passed through a decompression valve into a further gas, liquid separator or directly into a distillation unit or a plurality of distillation units. In both cases, dissolved gas, predominantly hydrogen, but also inert gases, for example nitrogen and methane, are discharged and preferably incinerated, which can generate energy. It is also possible first to use a separator and then a distillation unit or a plurality of distillation units. The pressure after the release is generally between standard pressure and 20 bar, preferably between standard pressure and 15 bar, more preferably between standard pressure and 10 bar. The liquid effluent from the separator is subsequently sent to the distillative workup and is referred to hereinafter as stream A and comprises generally methanol, propanol, butanol, water, gamma-butyrolactone, 2-methyl-1,4-butanediol, 1,4-butanediol, an acetal of 4-hydroxybutyraldehyde and 1,4-butanediol, acetal, pentanediols, for example 1,5-pentanediol and 2-methyl-1,5-pentanediol, salts, organic high boilers, and further, quantitatively insignificant secondary components.

The temperatures of the distillations described below are determined by the vapor pressures of the components present in the streams and the pressure set. The distillations preferably run with thermal integration in order to consume a minimum amount of energy.

To separate stream A, preference is given to using a plurality of distillation units. For example, low boilers such as methanol, propanol, butanol and water are removed from the 1,4-butanediol-containing product stream at pressures (absolute) between 0.5 and 20 bar, preferably between 0.8 and 10 bar. This removal can be effected in one distillation unit or in a plurality thereof. Preference is given to, in one distillation unit, first distilling off a mixture of methanol, propanol and butanol which also comprises water and then, in a further column or a plurality of further columns which preferably have thermal integration, distilling off the remaining water. The product stream comprising methanol, propanol and butanol and also water can either be incinerated or separated separately into the individual components, in order to use them, for example, as solvents in other processes. Methanol can, for example, be utilized in formaldehyde preparation. The water removed can, when it comprises a sufficiently low level of organic material, preferably be sent to a wastewater treatment.

The product stream which is obtained after the distillative removal of the water and low boilers is referred to hereinafter as B and comprises gamma-butyrolactone, 2-methyl-1,4-butanediol, 1,4-butanediol, acetal, pentanediols, salts, organic high boilers and further, quantitatively insignificant secondary components, and is treated further by distillation, for which there are several possibilities:

i) Stream B can be separated into volatile organic constituents, referred to hereinafter as stream C, comprising gamma-butyrolactone, 2-methyl-1,4-butanediol, 1,4-butanediol, acetal, pentanediols and further, quantitatively insignificant secondary components, and predominantly nonvolatile organic constituents which comprise the inorganic components. This is typically performed at a pressure (absolute) of from 0.005 to 1 bar, preferably between 0.01 and 0.7 bar, more preferably at from 0.02 to 0.4 bar, for example in a falling-film evaporator or a thin-film evaporator. The high boilers removed are incinerated, preferably together with salts present.

Stream C is also separated by distillation, which is done, for example, in a dividing wall column in which stream C is introduced into the column on one side of the dividing wall, while virtually pure 1,4-butanediol is drawn off on the other side of the dividing wall. A mixture consisting of predominantly gamma-butyrolactone with 1,4-butanediol and further, quantitatively insignificant components is drawn off via the top of the dividing wall column. This top product can be removed in its entirety, for example via the incineration, or be recycled into the process partly or in its entirety. In the latter case, the gamma-butyrolactone present can serve to regulate the pH. This top stream is preferably recycled into the hydrogenation stage.

The bottom stream of the dividing wall column comprises predominantly 1,4-butanediol and further products such as 2-methyl-1,4-butanediol, acetal and quantitatively insignificant components, and can be removed in its entirety, for example via the combustion, or be recycled into the process partly or in its entirety, for example added to stream A or B. The virtually pure 1,4-butanediol may, as such, already have saleable quality, but it may also be fine-purified in a further column in order to obtain 1,4-butanediol purities of >99.5%. In addition to a dividing wall column, at least two columns with top and bottom draw in each case, but also with side draw, are also possible. The pressures of the dividing wall column or of the alternative columns for purifying stream C or for fine-purifying the 1,4-butanediol are between 0.005 and 0.8 bar, preferably between 0.01 and 0.5 bar, more preferably between 0.02 and 0.2 bar.

ii) Stream B can also be purified by distillation, in which case this is done, for example, in at least two columns or in a dividing wall column, in which stream B is introduced into the column on one side of the dividing wall or into the first column when two columns are used, while virtually pure 1,4-butanediol is drawn off on the other side of the dividing wall or via side draw or via the top from the second column when two columns are used. A mixture consisting of predominantly gamma-butyrolactone with 1,4-butanediol and other, quantitatively insignificant products is drawn off via the top of the dividing wall column or from the first column when two columns are used. This top product can be removed in its entirety, for example via the combustion, or be recycled into the process partly or in its entirety. In the latter case, the gamma-butyrolactone present can serve to regulate the pH. This top stream is preferably recycled into the hydrogenation stage.

The bottom stream of the dividing wall column or the bottom stream of the second column when two columns are used comprises predominantly 1,4-butanediol, salts, high boilers and further products such as 2-methyl-1,4-butanediol, acetal and quantitatively insignificant products, and can be removed in its entirety, for example via the combustion, or preferably be separated, for example in a thin-film evaporator or in a thin-film evaporator, into high boilers and salts, and also a 1,4-butanediol-comprising stream which can be added, for example, to stream A or B. The virtually pure 1,4-butanediol may as such already have saleable quality, but it can also be fine-purified in a further column in order to obtain 1,4-butanediol purities of >99.5%. The pressures (absolute) of the dividing wall column for the purification of stream B or for the fine purification of the 1,4-butanediol are between 0.005 and 0.8 bar, preferably between 0.01 and 0.5 bar, more preferably between 0.02 and 0.2 bar. The pressures (absolute) of the falling-film evaporator or of the thin-film evaporator are from 0.005 to 1 bar, preferably between 0.01 and 0.7 bar, more preferably at 0.02 and 0.4 bar.

iii) Stream B can be separated in a column in such a way that a product stream consisting predominantly of gamma-butyrolactone, and additionally 1,4-butanediol and other, quantitatively insignificant components is drawn off via the top. This top product can be removed in its entirety, for example via the combustion, or be recycled into the process partly or in its entirety. In the latter case, the gamma-butyrolactone present can serve to regulate the pH. This top stream is preferably recycled into the hydrogenation stage. The bottom stream, referred to hereinafter as stream D, comprises 2-methyl, 1,4-butanediol, 1,4-butanediol, acetal and further, quantitatively insignificant secondary components, and nonvolatile organic constituents and also salts. This stream D can, for example, be separated in a falling-film evaporator or thin-film evaporator at pressures (absolute) between 0.005 to 1 bar, preferably between 0.01 and 0.7 bar, more preferably at 0.02 and 0.4 bar, into high boilers which comprise nonvolatile organic constituents and salts, and a stream comprising predominantly 1,4-butanediol. The 1,4-butanediol-comprising stream can be separated in a further column which be designed as a dividing wall column or as a normal side draw column, and pure 1,4-butanediol is withdrawn as a side draw in both cases. The pressures of the dividing wall column or side draw column are between 0.005 and 0.8 bar, preferably between 0.01 and 0.5 bar, more preferably between 0.02 and 0.2 bar. The top and bottom streams can be disposed of completely or partly or completely or partly be recycled, for example, into streams A, B and/or D, and comprise predominantly 1,4-butanediol.

iiii) Stream D can be separated in such a way that, in a column which may be designed as a dividing wall column or as a normal side draw column, pure 1,4-butanediol is withdrawn as a side draw in both cases. The pressures of the dividing wall column or side draw column are between 0.005 and 0.8 bar, preferably between 0.01 and 0.5 bar, more preferably between 0.02 and 0.2 bar. The top stream can be disposed of completely or partly or be completely or partly recycled, for example, into streams A and/or B, and comprises predominantly 1,4-butanediol. The bottom stream, which still comprises 1,4-butanediol, high boilers and salts, can, for example, be separated in a falling-film evaporator or thin-film evaporator at pressures (absolute) between 0.005 to 1 bar, preferably between 0.01 and 0.7 bar, more preferably at 0.02 and 0.4 bar, into high boilers which comprise nonvolatile organic constituents and salts, and a stream which comprises predominantly 1,4-butanediol and is added, for example, to streams A and/or B and/or D.

iiiii) Stream B can be separated in a column such that a stream E consisting of predominantly 1,4-butanediol, which also comprises gamma-butyrolactone, 2-methyl-1,4-butanediol and acetal, is obtained via the top, and a stream F which, as well as 1,4-butanediol, 2-methyl-1,4-butanediol, acetal, also comprises the high boilers and salts is obtained via the bottom. The top stream E is distilled in a further column, the top stream obtained being predominantly gamma-butyrolactone with 1,4-butanediol and other, quantitatively insignificant components. This top product can be removed in its entirety, for example via the incineration, or be recycled into the process partly or in its entirety. In the latter case, the gamma-butyrolactone present can serve to regulate the pH. This top stream is preferably recycled into the hydrogenation stage. Pure 1,4-butanediol is obtained via a side stream, but can also be drawn off as a bottom product. The side draw removal can be effected in liquid or gaseous form, either in the stripping section or in the rectifying section, or exactly in the middle of the column. The column has a number of theoretical plates between 30 and 200, preferably from 50 to 150. The bottom stream, which comprises predominantly 1,4-butanediol, can be drawn off as a pure product or can, for example, be fed to streams A, B and/or F. Stream F can be separated in a further column, in which case the top stream obtained is a mixture which comprises predominantly 1,4-butanediol, which can either be sent in its entirety to incineration or be fed partly or in its entirety, for example, to stream A, B and/or E. The bottom stream obtained is a stream which, as well as 1,4-butanediol, also comprises the high boilers and the salts. This bottom stream is preferably separated in a falling-film evaporator or thin-film evaporator at pressures (absolute) between 0.005 to 1 bar, preferably between 0.01 and 0.7 bar, more preferably at 0.02 and 0.4 bar, into high boilers which comprise nonvolatile organic constituents and salts, and a stream which comprises predominantly 1,4-butanediol and is added, for example, to streams A, B, D and/or E and/or F. The high boilers obtained are incinerated together with the salts.

The column types used in the distillation steps are common knowledge to those skilled in the art. They are, for example, packed columns, tray columns with sieve trays, dual-flow trays, bubble-cap trays, valve trays, etc.

The vacuum unit or units can be operated with various media, for example water. It has been found to be advantageous to operate them with 1,4-butanediol.

The pure 1,4-butanediol obtained by the above process variants usually has purities of >99.5%, typically >99.7%. Significant accompanying components are 2-methyl-1,4-butanediol and acetal. Since the acetal in particular is disruptive in the typical 1,4-butanediol uses, since it bears only one OH group, it may be advisable to further deplete this component. This can be achieved, for example, by admixing, for example, one of streams C or E or already purified 1,4-butanediol with a little water, and hydrogenating it over an Ni catalyst. This procedure is described, for example, in WO 97/36846. After removal of water, the reaction product can be introduced back into the process at a suitable point in the process, for example as stream C or E. In principle, stream C or E is interrupted by a hydrogenation stage in this procedure. This procedure allows particularly low-acetal 1,4-butanediol to be obtained. It then comprises typically less than 500 ppm of acetal.

It has been found to be advantageous that a particularly high 1,4-butanediol purity can be obtained when a very small amount of oxygen is present in the vacuum distillation. Particularly high purity means that a minimum level of monofunctional components and aldehyde derivatives, such as acetal, 4-hydroxybutyraldehyde or its cyclic hemiacetal and gamma-butyrolactone, are present. The molar ratio of oxygen to 1,4-butanediol in the vacuum columns does not, in accordance with the invention, exceed 1:500. The ratio is preferably below 1:1000, more preferably below 1:1500, especially preferably below 1:2500.

The inventive oxygen to butanediol ratios are achieved by preventing oxygen from remaining and the ingress of oxygen in the design and operation of the column or distillation unit. In accordance with the invention, it has been acknowledged that, preferably in the column in which the 1,4-butanediol is to be obtained as a pure product, an inventive oxygen to 1,4-butanediol ratio has to be observed.

The inventive oxygen-butanediol molar ratios are achieved by careful sealing of the columns with the aid of groove or spring seals; use of sealants such as silicone sealants, avoidance of flanges as are typically used for the temperature or pressure measuring points on columns, use of chambered columns or distillation units with purging of the chambers with inert gases, for example argon or nitrogen.

The amount of oxygen which is introduced into the columns can, for example, be determined before the feedstream is put into operation by measuring the amount of the offgas stream and its oxygen content downstream of the vacuum unit of each vacuum column, for example by gas chromatography. During operation, it should be noted that the oxygen content might be indicated as too low, since oxygen can actually be depleted by a reaction under these conditions. An important indication in this context can be given by the ratio of oxygen to nitrogen, which should correspond to that of the ambient air. A further means of determining the oxygen content is to evacuate the column without product feed, to isolate the column from the vacuum unit by closing a valve and to observe the rise in the pressure per unit time in the column. With knowledge of the column volume, the ingress of oxygen per unit time can be determined therefrom easily.

The 1,4-butanediol obtained by the above process variants usually has purities of >99.5%, typically >99.8%. The significant accompanying component is still 2-methyl-1,4-butanediol; the acetal, which is particularly undesired as a monoalcohol, lies generally below 0.1%, usually below 0.07%.

1,4-Butanediol finds use in industry in large amounts, for example in THF preparation or as a diol component in polyesters.

EXAMPLES

In the examples, the pressures stated are always absolute; the analysis of the hydrogenation effluents and of the pure butanediol is reported in GC area percent.

Example 1

In a reactor battery consisting of three cylindrical 10 m-long reactors with a diameter of 15 cm, filled with a catalyst (approx. 15% CuO, approx. 4% $Bi_2O_3$ on $SiO_2$) in the form of 0.5-2 mm spall, prepared according to DE-A 26 02 418, which was operated both with cycle gas and with liquid circulation in upward mode (feed to circulation 10:1), 20 kg/h 32% aqueous formaldehyde and 2.8 kg/h of acetylene were reacted at 5 bar and from 70 to 90° C. at a pH of 6. The reaction product of the first reactor was conveyed into the second reactor and that of the second reactor into the third reactor. In this way, >95% of the formaldehyde and of the acetylene were converted to 1,4-butynediol. The pH of the reaction was controlled such that the pH was measured downstream of each reactor and, if required, small amounts of 1% aqueous NaOH solution were metered in. The reaction effluent of the third reactor was separated into gas and liquid phase in a separator. The liquid phase comprised approx. 50% by weight of butynediol, 1.3% by weight of propynol, 0.5% by weight of formaldehyde, 0.5% by weight of methanol, dissolved acetylene and several 100 ppm of nonvolatile oligomers, polymers and catalyst constituents, and also <0.5% other impurities and water. The gas phase, which comprised essentially acetylene, was recycled predominantly as cycle gas; 1% of the gas stream was discharged. The liquid effluent of the separator was passed into a column in which water, formaldehyde, methanol and propynol were removed (approx. 1 kg) via the top at 0.2 bar absolute and bottom temperature 90° C., and recycled into the reaction.

The bottom effluent was passed continuously into an intermediate buffer in which the mean residence time was 10 h at 60° C. and 1 bar (absolute). The butynediol-containing solution was withdrawn from this intermediate buffer and hydrogenated in a two-stage reactor battery with hydrogen over an Ni catalyst according to EP-A 394 841 in the form of 3×3 mm tablets (approx. 38% by weight of Ni, approx. 12% by weight of Cu on $ZrO2/MoO3$). The molar ratio of fresh hydrogen to 1,4-butynediol was 2.1:1. The first hydrogenation reactor (length 10 m, diameter 10 cm) was operated with liquid circulation for cooling in upward mode at reactor inlet pressure 250 bar and 120-140° C. To adjust the pH to approx. 7.2, 1% aqueous NaOH or gamma-butyrolactone was metered into the feed. The second reactor (length 10 m, diameter 5 cm) was operated in trickle mode of 140-160 to 140 to 175° C. at 250 bar. The effluent was separated in a separator into liquid phase and gas phase, and the gas phase was recycled by means of a cycle gas compressor. Approx. 1% of the amount of the fresh gas was discharged continuously from the gas stream as offgas and incinerated. The hydrogenation effluent was decompressed to approx. 5 bar and the gas stream released was likewise sent to the combustion. Subsequently, the degassed hydrogenation effluent was separated into the individual constituents in a battery of columns. In a first column, low boilers such as methanol, propanol and n-butanol were removed via the top with water at approx. 5 bar and a bottom temperature of approx. 170° C. and sent to incineration. The bottom stream passed into a second column in which quite predominantly water was distilled off via the top, likewise at approx. 0.3 bar and bottom temperature approx. 130° C. The bottom stream of the second column was separated in a third column at approx. 0.15 bar and bottom temperature approx. 175° C. such that predominantly 1,4-butanediol together with gamma-butyrolactone, 2-methyl-1,4-butanediol, acetal, pentanediols and a few further, quantitatively insignificant components were distilled off via the top. This top stream was separated in a fourth column, which was operated at approx. 0.04 bar and bottom temperature approx. 165° C., into a top stream which, as well as 1,4-butanediol, comprised predominantly gamma-butyrolactone, a side stream which consisted of predominantly 1,4-butanediol, and a bottom stream which likewise consisted of predominantly 1,4-butanediol and was fed into the bottom stream of the third column. The bottom stream of the third column, together with that of the fourth column, was separated in a fifth column at approx. 0.05 bar and bottom temperature 170° C. such that the top stream, which comprised predominantly 1,4-butanediol, was recycled into the feed of the third column, while the bottom stream, which, as well as a little 1,4-butanediol, comprised high boilers and salts, was discharged and incinerated.

Course of the hydrogenation and purity of the 1,4-butanediol after purification

After 24 h, in the hydrogenation effluent of the first reactor (calculated without water), approx. 94% 1,4-butanediol, 0.1% 1,4-butenediol, 0.05% gamma-butyrolactone, 0.05% 2-methyl-1,4-butanediol, 1.5% methanol, 2.5% n-propanol, 1.1% n-butanol, 0.07% acetal, 0.1% pentanediols and a multitude of quantitatively minor components were found. The pressure drop (reactor outlet pressure minus reactor inlet pressure) was 2.5 bar. In the outlet of the post-hydrogenation reactor, (calculated without water), approx. 94.2% 1,4-butanediol, 0.04% gamma-butyrolactone, 0.06% 2-methyl-1,4-butanediol, 1.6% methanol, 2.5% n-propanol, 1.2% n-butanol, 0.04% acetal and a multitude of quantitatively minor components were found.

The pure 1,4-butanediol had the composition of 99.90% 1,4-butanediol, 0.05% 2-methyl-1,4-butanediol, 0.04% acetal and several quantitatively insignificant components.

After 12 weeks of operating time of the hydrogenation, in the hydrogenation effluent of the first reactor (calculated without water), approx. 91% 1,4-butanediol, 1.1% 1,4-butenediol, 0.05% 1,4-butynediol, 0.08% gamma-butyrolactone, 0.08% 2-methyl-1,4-butanediol, 1.5% methanol, 2.3% n-propanol, 2.9% n-butanol, 0.15% acetal and a multitude of quantitatively minor components were found. The pressure drop (reactor outlet pressure minus reactor inlet pressure) was 4.5 bar. In the outlet of the second reactor, (calculated without water), approx. 91.2% 1,4-butanediol, 0.05% gamma-butyrolactone, 0.09% 2-methyl-1,4-butanediol, 1.7% methanol, 2.5% n-propanol, 3.0% n-butanol, 0.13% acetal and a multitude of quantitatively minor components were found.

The pure 1,4-butanediol had the composition of 99.80% 1,4-butanediol, 0.08% 2-methyl-1,4-butanediol, 0.1% acetal and several quantitatively minor components.

After these 12 weeks of operating time, the first hydrogenation reactor was flushed with water and the catalyst was then deinstalled under water and washed to free it of adhering impurities with water and then reinstalled. Thereafter, virtually the same hydrogenation profile and 1,4-butanediol purity as before were established. It was possible to pass through a total of 4 wash cycles until the hydrogenation result slowly became poorer.

Comparative Example 1

Example 1 was repeated, with the difference that the effluent from the reaction of acetylene with formaldehyde was not intermediately buffered but rather converted immediately in the hydrogenation. At the start, everything was as in the inventive example, except that the values as attained after 12 weeks in the inventive example were attained as early as after 8 weeks (hydrogenation effluent of the first reactor (calculated without water) approx. 91% 1,4-butanediol, 1.1% 1,4-butenediol, 0.06% 1,4-butynediol, 0.08% gamma-butyrolactone, 0.08% 2-methyl-1,4-butanediol, 1.4% methanol, 2.3% n-propanol, 2.9% n-butanol, 0.16% acetal and a multitude of quantitatively minor components. The pressure drop (reactor outlet pressure minus reactor inlet pressure) was 4.6 bar. In the outlet of the second hydrogenation reactor, (calculated without water), approx. 91.2% 1,4-butanediol, 0.05% gamma-butyrolactone, 0.09% 2-methyl-1,4-butanediol, 1.6% methanol, 2.5% n-propanol, 3.0% n-butanol, 0.14% acetal and a multitude of quantitatively minor components were found. The pure 1,4-butanediol had the composition of 99.80% 1,4-butanediol, 0.08% 2-methyl-1,4-butanediol, 0.1% acetal and a plurality of quantitatively insignificant components.)

After deinstallation, washing and reinstallation of the hydrogenation catalyst, the starting values were not quite attained again, so that the catalyst had to be washed again as early as after 7 weeks in the second phase.

Example 2

Example 1 was repeated, but with the following changes: intermediate buffering at 75° C. for 2 hours; hydrogenation catalyst with the composition of approx. 56% Ni on $SiO_2/Al_2O_3$.

After 24 h, in the hydrogenation effluent of the first reactor (calculated without water), approx. 93.5% 1,4-butanediol, 0.3% 1,4-butenediol, 0.05% gamma-butyrolactone, 0.05% 2-methyl-1,4-butanediol, 1.5% methanol, 2.5% n-propanol, 1.1% n-butanol, 0.1% acetal, 0.1% pentanediols and a multitude of quantitatively minor components were found. The pressure drop (reactor outlet pressure minus reactor inlet pressure) was 2.4 bar. In the outlet of the post-hydrogenation reactor, (calculated without water) approx. 94.0% 1,4-butanediol, 0.04% gamma-butyrolactone, 0.06% 2-methyl-1,4-butanediol, 1.4% methanol, 2.1% n-propanol, 1.3% n-butanol, 0.06% acetal and a multitude of quantitatively minor components were found.

The pure 1,4-butanediol had the composition of 99.87% 1,4-butanediol, 0.05% 2-methyl-1,4-butanediol, 0.07% acetal and a plurality of quantitatively insignificant components were found.

After 10 weeks of operating time of the hydrogenation, in the hydrogenation effluent of the first reactor (calculated without water), approx. 90.5% 1,4-butanediol, 1.3% 1,4-butenediol, 0.07% 1,4-butynediol, 0.06% gamma-butyrolactone, 0.09% 2-methyl-1,4-butanediol, 1.5% methanol, 2.2% n-propanol, 2.9% n-butanol, 0.16% acetal and a multitude of quantitatively minor components were found. The pressure drop (reactor outlet pressure minus reactor inlet pressure) was 4.6 bar. In the outlet of the second hydrogenation reactor, (calculated without water) approx. 92.2% 1,4-butanediol, 0.05% gamma-butyrolactone, 0.09% 2-methyl-1,4-butanediol, 1.5% methanol, 2.5% n-propanol, 3.0% n-butanol, 0.14% acetal and a multitude of quantitatively minor components were found.

The pure 1,4-butanediol had the composition of 99.80% 1,4-butanediol, 0.08% 2-methyl-1,4-butanediol, 0.11% acetal and a plurality of quantitatively minor components.

After these 10 weeks of operating time, the first hydrogenation reactor was flushed with water and the catalyst was then deinstalled under water and washed with water to free of it of adhering impurities and then reinstalled. Thereafter, virtually the same hydrogenation profile and 1,4-butanediol purity were established as before. It was possible to pass through a total of 5 wash cycles until the hydrogenation result slowly became poorer.

Comparative Example 2

For the workup, technical 1,4-butanediol in the form of a 54% by weight aqueous solution, which had been obtained by hydrogenating technical 1,4-butynediol over an Ni catalyst according to example 1 of EP-A 482 445 was used and had the following composition (calculated without water): approx. 94% 1,4-butanediol, 0.05% gamma-butyrolactone, 0.6% 2-methyl-1,4-butanediol, 1.5% methanol, 2.3% n-propanol, 1.1% n-butanol, 0.07% acetal, 0.1% pentanediols and a multitude of quantitatively minor components.

The hydrogenation effluent was separated into the individual constituents in a battery of columns. In a first column, low boilers such as methanol, propanol and n-butanol were removed via the top with water at approx. 5 bar and a bottom temperature of approx. 170° C. and sent to incineration. The bottom stream passed into a second column in which quite predominantly water was distilled off via the top, likewise at approx. 0.3 bar and bottom temperature approx. 130° C. The bottom stream of the second column was separated in a third column at approx. 0.15 bar and bottom temperature approx. 175° C. such that predominantly 1,4-butanediol together with gamma-butyrolactone, 2-methyl-1,4-butanediol, acetal, pentanediols and a few further, quantitatively insignificant components were distilled off via the top. This top stream was separated in a fourth column, which was operated at approx. 0.04 bar and bottom temperature approx. 165° C., into a top stream which, as well as 1,4-butanediol, comprised predominantly gamma-butyrolactone, a side stream which consisted of pure 1,4-butanediol, and a bottom stream which likewise consisted of predominantly 1,4-butanediol and was fed into the bottom stream of the third column. The bottom stream of the third column, together with that of the fourth column, was separated in a fifth column at approx. 0.05 bar and bottom temperature 170° C. such that the top stream, which comprised predominantly 1,4-butanediol, was recycled into the feed of the third column, while the bottom stream, which, as well as a little 1,4-butanediol, comprised high boilers and salts, was discharged and incinerated.

The pure 1,4-butanediol had the composition of 99.5% 1,4-butanediol, 0.1% 2-methyl-1,4-butanediol, 0.14% acetal, 0.05% 4-hydroxybutyraldehyde and its cyclic hemiacetal, 0.09% gamma-butyrolactone and a plurality of further quantitatively minor components.

The fourth column of the battery, from which the 1,4-butanediol was obtained in pure form, had a measurement system for the gas stream and the oxygen content present therein. The amounts of oxygen found in the offgas stream by GC analysis of the offgas stream of the vacuum pump was such as to indicate that at least a molar ratio of oxygen to 1,4-butanediol of 1:350 was present in the column.

Example 3

Comparative example 1 was repeated, except that all flanges and stubs (for thermometers and pressure meters) of the column battery were sealed with silicone sealant. Thereafter, the molar ratio of oxygen to 1,4-butanediol in the offgas of the fourth column fell to approx. 1:1000. The resulting pure 1,4-butanediol subsequently exhibited a purity of 99.8% 1,4-butanediol, 0.1% 2-methyl-1,4-butanediol, 0.05% acetal, 4-hydroxybutyraldehyde and its cyclic hemiacetal undetectable, 0.01% gamma-butyrolactone and a plurality of further quantitatively minor components.

The invention claimed is:

1. An integrated process for continuously preparing 1,4-butanediol, which comprises:
   (I) reacting formaldehyde with acetylene in the presence of a copper catalyst at a pH of from 5 to 8 and a molar ratio of formaldehyde to acetylene of at most 2:1,
   (II) intermediately buffering the resulting butynediol-containing aqueous mixture for from 0.1 to 100 h,
   (III) hydrogenating the mixture obtained after the intermediate buffering and
   (IV) distilling the hydrogenation product obtained from said hydrogenating to obtain 1,4-butanediol.

2. The integrated process according to claim 1, wherein the intermediate buffering is performed at a temperature of from 20 to 100° C. and at a pressure of from 0.8 to 20 bar.

3. The integrated process according to claim 1, wherein the intermediate buffering is performed at a temperature of from 40 to 90° C. and at a pressure of from 0.8 to 20 bar.

4. The integrated process according to claim 1, wherein the intermediate buffering is performed at a temperature of from 50 to 80° C. and at a pressure of from 0.8 to 20 bar.

5. The integrated process according to claim 1, wherein the intermediate buffering is performed at a mean residence time of from 0.5 to 50 h.

6. The integrated process according to claim 1, which further comprises removing acetylene, formaldehyde, water and by-products in at least one distillation which occurs before the intermediate buffering.

7. The integrated process according to claim 6, wherein the distillation is performed at a temperature of from 80 to 100° C. and at a pressure of from 0.1 to 1 bar.

8. The integrated process according to claim 1, which further comprises removing acetylene, formaldehyde, water and by-products in at least one distillation which occurs after the intermediate buffering.

9. The integrated process according to claim 8, which further comprises a second buffering which occurs after the distillation and before the hydrogenating.

10. The integrated process according to claim 1, wherein free acetylene is present through the entire reaction zone in said reacting.

11. The integrated process according to claim 1, wherein said hydrogenating is performed at a pH of from 6 to 9.

12. The integrated process according to claim 1, wherein said hydrogenating is performed in at least two stages.

13. The integrated process according to claim 1, wherein the catalyst of the hydrogenation (stage III) is washed after use and then reinstalled.

14. The integrated process according to claim 1, which further comprises at least one of removing, washing, and reinstalling a catalyst which is present during said hydrogenating.

15. The integrated process according to claim 2, wherein the intermediate buffering is performed at a mean residence time of from 0.5 to 50 h.

16. The integrated process according to claim 3, wherein the intermediate buffering is performed at a mean residence time of from 0.5 to 50 h.

17. The integrated process according to claim 2, which further comprises removing acetylene, formaldehyde, water and by-products in at least one distillation which occurs before the intermediate buffering.

18. The integrated process according to claim 3, which further comprises removing acetylene, formaldehyde, water and by-products in at least one distillation which occurs before the intermediate buffering.

19. The integrated process according to claim 4, which further comprises removing acetylene, formaldehyde, water and by-products in at least one distillation which occurs before the intermediate buffering.

20. The integrated process according to claim 5, which further comprises removing acetylene, formaldehyde, water and by-products in at least one distillation which occurs before the intermediate buffering.

* * * * *